(12) United States Patent
Ceniccola

(10) Patent No.: US 9,962,219 B2
(45) Date of Patent: May 8, 2018

(54) SURGICAL INSTRUMENT WITH INTERCHANGEABLE MICRO-TIPS

(71) Applicant: Covidien LP, Mansfield, MA (US)

(72) Inventor: Anthony Ceniccola, Hamden, CT (US)

(73) Assignee: Covidien LP, Mansfield, MA (US)

( * ) Notice: Subject to any disclaimer, the term of this patent is extended or adjusted under 35 U.S.C. 154(b) by 165 days.

(21) Appl. No.: 14/737,863

(22) Filed: Jun. 12, 2015

(65) Prior Publication Data

US 2016/0361108 A1 Dec. 15, 2016

(51) Int. Cl.
*A61B 18/14* (2006.01)
*A61B 17/00* (2006.01)
*A61B 34/00* (2016.01)
*A61B 50/20* (2016.01)
*A61B 50/30* (2016.01)
*A61B 18/00* (2006.01)

(52) U.S. Cl.
CPC ........ *A61B 18/14* (2013.01); *A61B 17/00234* (2013.01); *A61B 18/1492* (2013.01); *A61B 34/70* (2016.02); *A61B 50/20* (2016.02); *A61B 50/30* (2016.02); *A61B 2017/00318* (2013.01); *A61B 2017/00464* (2013.01); *A61B 2017/00473* (2013.01); *A61B 2017/00477* (2013.01); *A61B 2017/00876* (2013.01); *A61B 2018/00172* (2013.01); *A61B 2018/00196* (2013.01); *A61B 2018/1475* (2013.01); *A61B 2018/1495* (2013.01); *A61B 2050/21* (2016.02); *A61B 2050/3008* (2016.02)

(58) Field of Classification Search
CPC . A61B 2018/1495; A61B 18/14; A61M 25/04
See application file for complete search history.

(56) References Cited

U.S. PATENT DOCUMENTS

| 6,358,241 B1 | 3/2002 | Shapeton et al. |
| 8,137,345 B2 | 3/2012 | McNall, III et al. |
| 2005/0283137 A1* | 12/2005 | Doyle ................ A61B 17/1222 606/1 |
| 2006/0247616 A1* | 11/2006 | Edwards ................ A61N 5/045 606/41 |
| 2012/0265196 A1* | 10/2012 | Turner ........... A61B 17/320092 606/34 |
| 2013/0035671 A1* | 2/2013 | Brand ................ A61B 1/00131 606/1 |

* cited by examiner

*Primary Examiner* — Daniel Fowler
*Assistant Examiner* — Sean W Collins

(57) ABSTRACT

A surgical instrument includes a housing, a shaft extending from the housing, and an end effector assembly that is disposed at a distal end of the shaft. The end effector assembly includes a tubular portion, a connection arm, and a toolbox. The tubular portion defines a lumen and the connection arm is extendable from the lumen. The toolbox has a micro-tip that is configured to be selectively secured to a connection tip of the connection arm. The toolbox has a transport configuration where the toolbox is disposed within the lumen and a deployed configuration where the toolbox is disposed entirely outside of the lumen.

20 Claims, 9 Drawing Sheets

SURGICAL INSTRUMENT WITH INTERCHANGEABLE MICRO-TIPS

BACKGROUND

1. Technical Field

The present disclosure relates to surgical instruments and, more specifically, to surgical instruments having interchangeable micro tips.

2. Discussion of Related Art

Electrosurgical instruments are widely used by surgeons. Electrosurgery involves application of high-frequency electrical current to a surgical site to cut, ablate, coagulate, cauterize or seal tissue.

The basic purpose of both monopolar and bipolar electrosurgery is to produce heat to achieve the desired tissue/clinical effect. In monopolar electrosurgery, devices use an instrument with a single, active electrode to deliver energy from an electrosurgical generator to tissue, and a patient return electrode or pad that is attached externally to the patient (e.g., a plate positioned on the patient's thigh or back) as the means to complete the electrical circuit between the electrosurgical generator and the patient. When the electrosurgical energy is applied, the energy travels from the active electrode, to the surgical site, through the patient and to the return electrode.

In bipolar electrosurgery, the electrosurgical device includes two electrodes that are located in proximity to one another for the application of current between their surfaces. Bipolar electrosurgical current travels from one electrode, through the intervening tissue to the other electrode to complete the electrical circuit. Bipolar electrosurgical instruments utilize two generally opposing electrodes that are both electrically coupled to an electrosurgical generator. Each electrode is charged to a different electric potential.

By utilizing an electrosurgical instrument, a surgeon can use electrosurgical energy to cauterize, coagulate/desiccate, cut tissue, and/or simply reduce or slow bleeding by controlling the intensity, frequency, and duration of the electrosurgical energy applied to the tissue.

Some electrosurgical instruments include a fixed probe which delivers electrosurgical energy in a manner determined by the shape of the fixed probe. During a surgical procedure with such an electrosurgical instrument, the electrosurgical instrument is manipulated within a surgical site to position the fixed probe adjacent targeted tissue. Alternatively, another instrument may be used to draw targeted tissue to the fixed probe. In addition, the electrosurgical instrument may be removed from a surgical site to change the tip and thus, the shape of the fixed probe and the manner of the delivery of electrosurgical energy.

There is a need for electrosurgical instruments that include a probe which may vary in shape without being removed from a surgical site. In addition, there is a need for electrosurgical instruments that may draw targeted tissue towards a fixed probe without an additional surgical instrument.

SUMMARY

Surgical instruments in accordance with the present disclosure include a deployable toolbox that includes one or more micro-tips that are selectively secured to a connection arm of the surgical instrument. The surgical instrument also includes an energy tip for selectively delivering electrosurgical energy to tissue.

In an aspect of the present disclosure, a surgical instrument includes a housing, a shaft extending from the housing, and an end effector assembly disposed at a distal end of the shaft. The end effector assembly includes a tubular portion, a connection arm, and a tool box. The tubular portion defines a lumen and the connection arm is extendable from the lumen. The connection arm has a connection tip. The toolbox includes a micro-tip that is configured to be selectively secured to the connection tip of the connection arm. The toolbox has a transport configuration where the toolbox is disposed within the lumen of the tubular portion and a deployed configuration where the toolbox is disposed entirely outside of the lumen.

In aspects, in the deployed configuration of the toolbox, a connection end of the micro-tip is engaged by the connection tip of the connection arm. The connection tip of the connection arm may be activated to secure the connection tip to the connection end. The connection tip may include an electromagnet or a vacuum passage. The micro-tip may be removable from the toolbox. The toolbox may include a plurality of micro-tips which are each selectively securable to the connection arm.

In some aspects, the connection arm is moveable within six degrees of freedom. The housing may include a control interface for manipulating the connection arm. The connection arm may secure the toolbox in the transport configuration. The connection arm may be extendable to transition the toolbox from the transport configuration to the deployed configuration. The connection arm may be retractable to transient the toolbox from the deployed configuration to the transport configuration.

In particular aspects, the end effector includes a finger that distally extends from the tubular portion to an energy tip that is configured to deliver electrosurgical energy to tissue. The connection arm may be configured to return electrosurgical energy from the energy tip when the micro-tip is coupled to the connection tip.

In another aspect of the present disclosure, a surgical system includes an electrosurgical energy source, a surgical instrument, and an end effector assembly. The surgical instrument includes a housing and a shaft that extends from the housing. The end effector assembly is disposed at a distal end of the shaft and includes a tubular portion, a finger, a connection arm, and a toolbox. The tubular portion defines a lumen. The finger extends distally from the tubular portion and includes an energy tip. The energy tip is in electrical communication with the electrosurgical energy source and is configured to deliver electrosurgical energy to tissue. The connection arm is extendable from the lumen of the tubular portion and has a connection tip. The toolbox has a micro-tip that is configured to be selectively secured to the connection tip of the connection arm. The toolbox has a transport configuration where the toolbox is disposed within the lumen of the tubular portion and a deployed configuration where the toolbox is disposed entirely outside of the lumen.

In aspects, the end effector assembly is configured to deliver electrosurgical energy in a bipolar manner. The connection arm may be configured to return electrosurgical energy from the energy tip to the electrosurgical energy source when the micro-tip is secured to the connection tip.

In another aspect of the present disclosure, a method for treating tissue includes extending a connection arm to deploy a toolbox from a transport configuration, removing a micro-tip from the toolbox with the connection arm, manipulating the connection arm to position targeted tissue adjacent an energy tip, and delivering electrosurgical energy to the targeted tissue with the energy tip. Extending the connection arm includes extending the connection arm from a lumen that is defined by a tubular portion of an end effector. In the transport configuration, the toolbox is disposed within the lumen and in the deployed configuration, the toolbox is disposed outside of the lumen.

In aspects, the method includes retracting the connection arm into the lumen to return the toolbox to the transport configuration. The method may include activating a connection tip of the connection arm to secure the toolbox to the connection tip before retracting the connection arm into the lumen. Removing the micro-tip from the toolbox may include engaging a connection end of the micro-tip with a connection tip of the connection arm and activating the connection end to secure the micro-tip to the connection tip.

Further, to the extent consistent, any of the aspects described herein may be used in conjunction with any or all of the other aspects described herein.

BRIEF DESCRIPTION OF THE DRAWINGS

Various aspects of the present disclosure are described hereinbelow with reference to the drawings, which are incorporated in and constitute a part of this specification, wherein.

DETAILED DESCRIPTION

Figure 1:
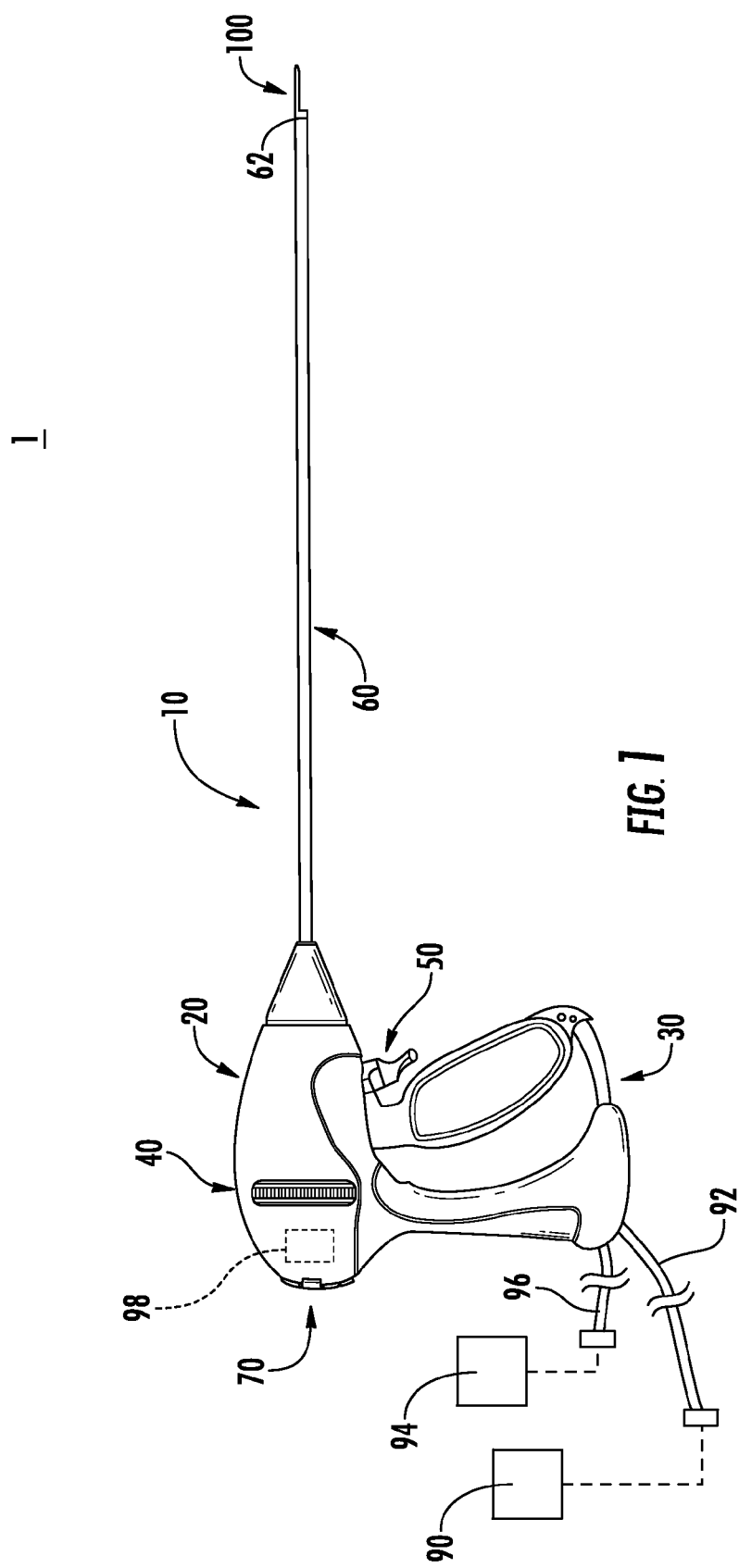
FIG. 1 is a side view of an electrosurgical instrument provided in accordance with the present disclosure and a schematic view of an electrosurgical surgical system.

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" refers to the portion of the device or component thereof that is closest to the clinician and the term "distal" refers to the portion of the device or component thereof that is farthest from the clinician.

Referring now to FIG. 1, an electrosurgical system 1 is provided in accordance with the present disclosure and includes an electrosurgical instrument 10 and an electrosurgical energy source 90. The electrosurgical instrument 10 is provided in accordance with the present disclosure and includes a housing 20, a handle assembly 30, a rotatable assembly 40, a trigger assembly 50, a shaft 60, and an end effector assembly 100. The shaft 60 extends from the housing 20 to a distal end 62. The end effector assembly 100 is supported at the distal end 62 of the shaft 60.

The electrosurgical energy source 90 is in electrical communication with the end effector assembly 100 to selectively deliver energy to targeted tissue with the end effector assembly 100. Specifically, the electrosurgical instrument 10 includes a cable 92 that connects to the electrosurgical energy source 90. Alternatively, the electrosurgical energy source 90 may be disposed on or within the housing 20.

Figure 2:
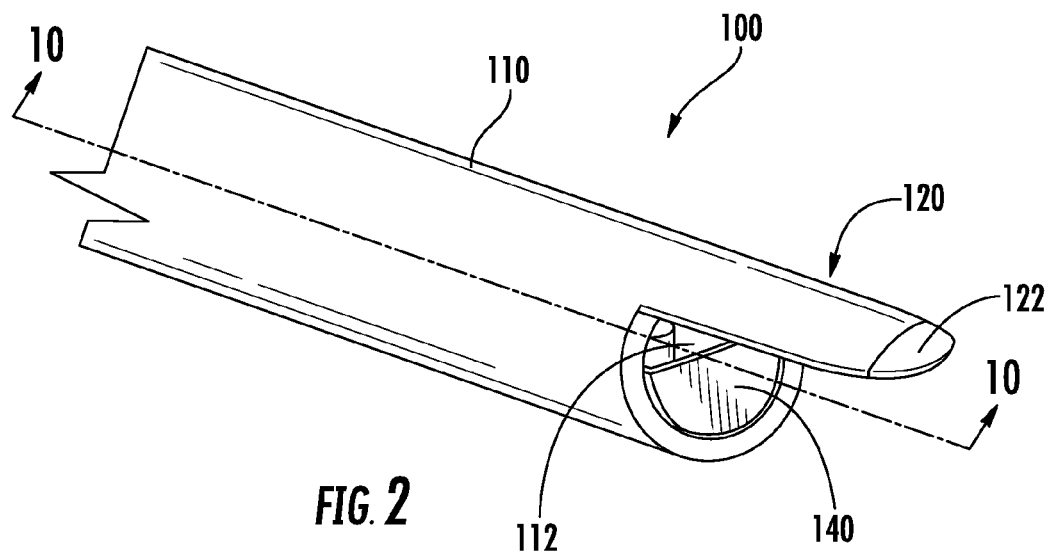
FIG. 2 is an enlarged perspective view of an end effector of the electrosurgical instrument of FIG. 1 with a toolbox in a transport configuration.
Figure 3:
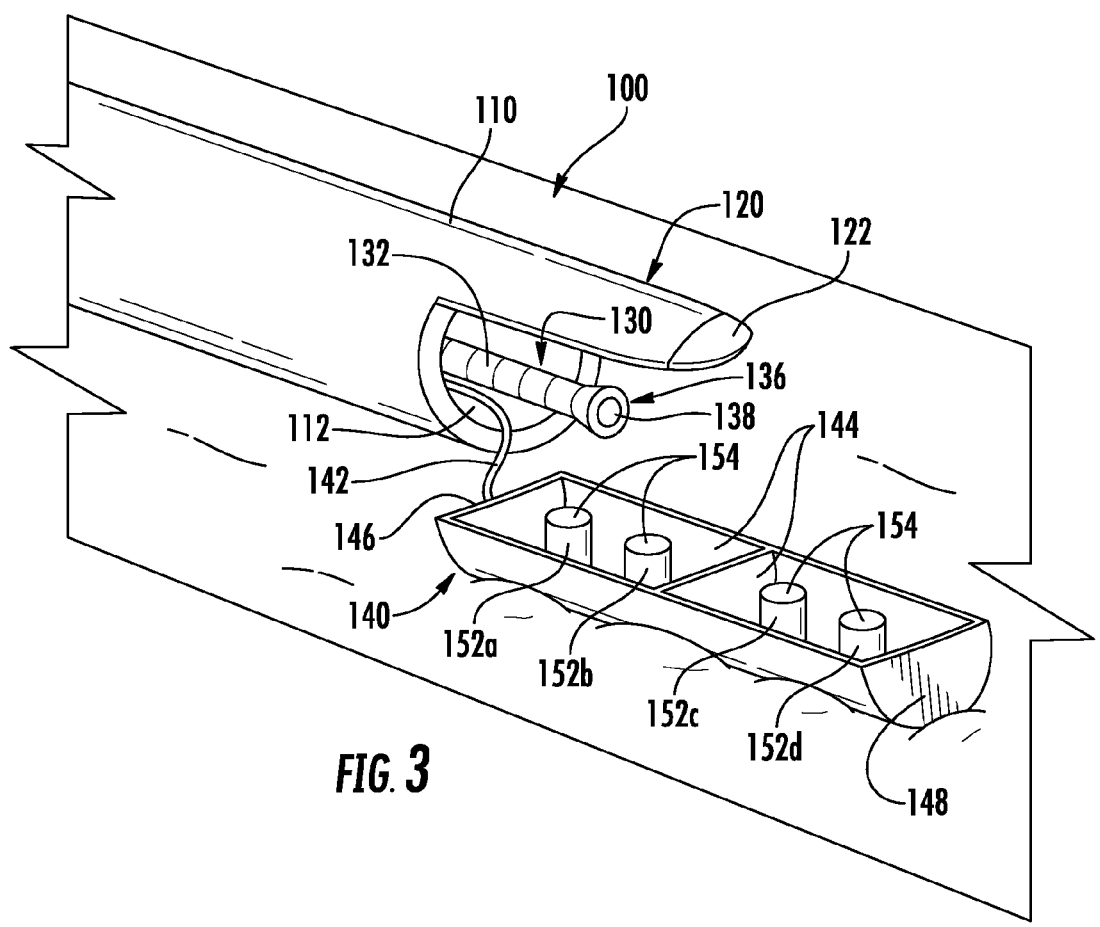
FIG. 3 is a perspective view of the end effector of the electrosurgical instrument of FIG. 2 positioned at a surgical site with the toolbox in a deployed configuration.

Referring now to FIGS. 2 and 3, the end effector assembly 100 includes a tubular portion 110, a finger 120, a connection arm 130, and a toolbox 140. The tubular portion 110 defines a lumen 112 that receives the toolbox 140. The finger 120 extends distally from the tubular portion 110 to an energy tip 122. The energy tip 122 is in electrical communication with the electrosurgical energy source 90 to deliver electrosurgical energy to targeted tissue as detailed below. The connection arm 130 is disposed within the lumen 112 of the tubular portion 110 and includes a flexible body 132 and a connection tip 136. Portions of the connection arm 130 may be rigid, semi-rigid, or flexible. The toolbox 140 defines storage wells 144 which releasably secure a plurality of micro-tips 152a-d therein. Each of the plurality of micro-tips 152a-d has a connection portion 153 (FIG. 4) which includes a connection end 154 for selectively securing the respective micro-tip 152a-d to the connection tip 136 of the connection arm 130 as detailed below.

As shown in FIG. 2, the toolbox 140 has a transport configuration where the toolbox 140 is disposed within the lumen 112 of the tubular portion 110. In the transport configuration, the connection tip 136 (FIG. 3) of the connection arm 130 may engage a proximal wall 146 (FIG. 3) of the toolbox 140 to secure the toolbox 140 within the lumen 112. The connection tip 136 is electromagnetic and the proximal wall 146 of the toolbox 140 is constructed of a magnetizable material such that when the connection tip 136 is activated (i.e., electrical energy is supplied to the connection tip 136) the connection tip 136 magnetically engages the proximal wall 146. This magnetic engagement of the connection tip 136 and the proximal wall 146 of the toolbox 140 secures the toolbox 140 in the transport configuration. It will be appreciated that the electrosurgical energy source 90 may be configured to compensate for a magnetic field generated by activating the connection tip 136.

Additionally or alternatively, the connection arm 136 may include a vacuum passage 138 therethrough which is in communication with vacuum source 94 through a vacuum hose 96 that selectively provides a vacuum through the vacuum passage 138. In such embodiments, the connection tip 136 may be coupled to the proximal wall 146 of the toolbox 140 by providing a vacuum to the vacuum passage 138 when the connection tip 136 is engaged with the proximal wall 146. It will be appreciated that in such embodiments, the proximal wall 146 need not be constructed of a magnetizable material.

As shown in FIG. 3, the toolbox 140 has a deployed configuration where the toolbox 140 is disposed outside of the lumen 112 of the tubular portion 110. As shown, the toolbox 140 is supported by tissue within a body cavity of a patient. The tubular portion 110 may include a tether 142 that is secured at one end to the interior of the lumen 112 and at the other end to the proximal wall 146 of the toolbox 140 such that toolbox 140 is secured to the tubular portion 110. The connection arm 130 may be extended from the lumen 112 to deploy or move the toolbox 140 from the transport configuration to the deployed configuration. The connection arm 130 may be extended with the connection tip 136 deactivated such that as the toolbox 140 is deployed from within the lumen 112, the toolbox 140 separates from the connection tip 136. Alternatively, the connection arm 130 may be extended with the connection tip 136 activated such that the proximal wall 146 of the toolbox 140 is magnetically coupled to the connection tip 136 to support the toolbox 140 as the connection arm 130 is extended. When the toolbox 140 is outside of the lumen 112, the connection arm 130 may be used to position the toolbox 140 within a body cavity of a patient before deactivating the connection tip 136 to release the proximal wall 146 of the toolbox 140. When the toolbox 140 is in the deployed configuration, the storage wells 144 of the toolbox 140 are accessible with the connection arm 130.

Figure 4:
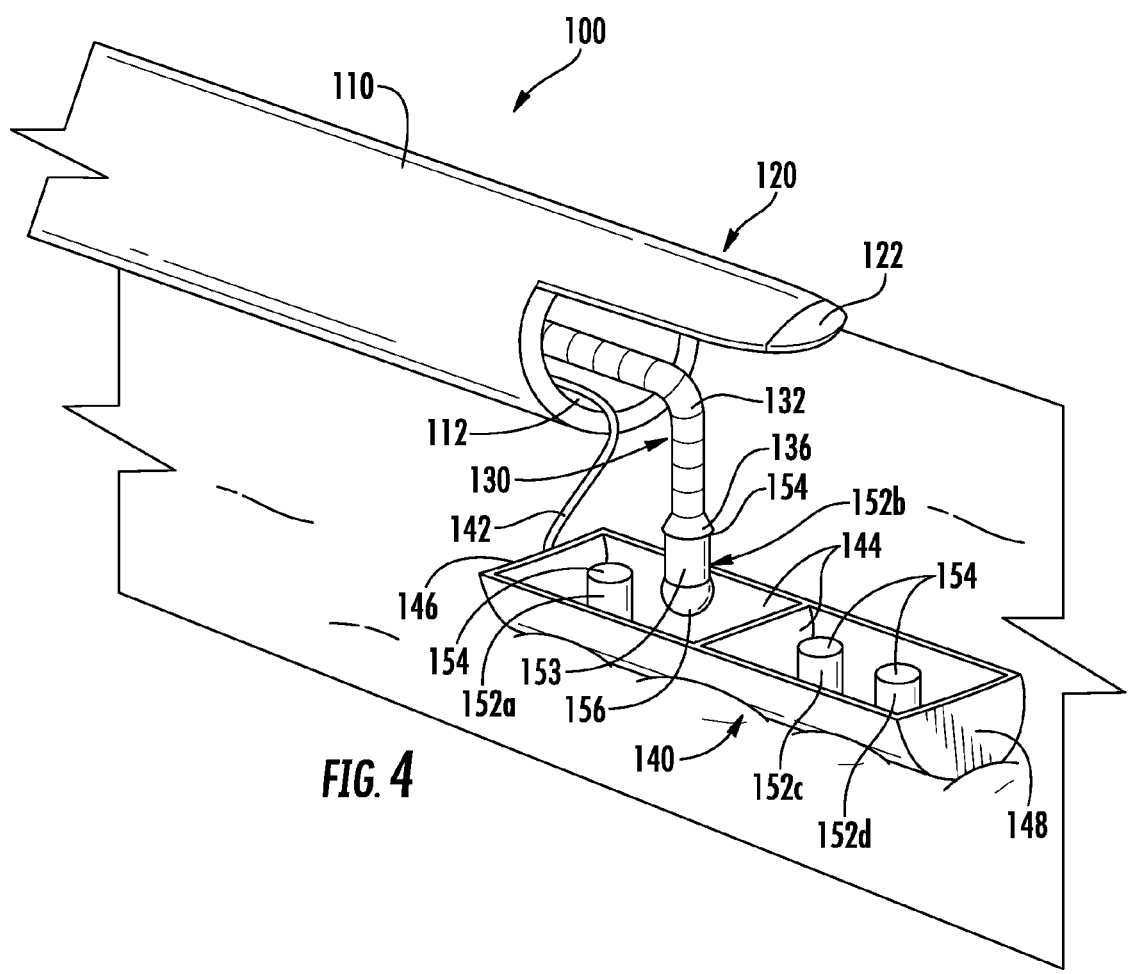
FIG. 4 is a perspective view of the end effector of the electrosurgical instrument of FIG. 3 with a connection arm of the end effector engaged with a connection end of a micro-tip of the toolbox.
Figure 5:
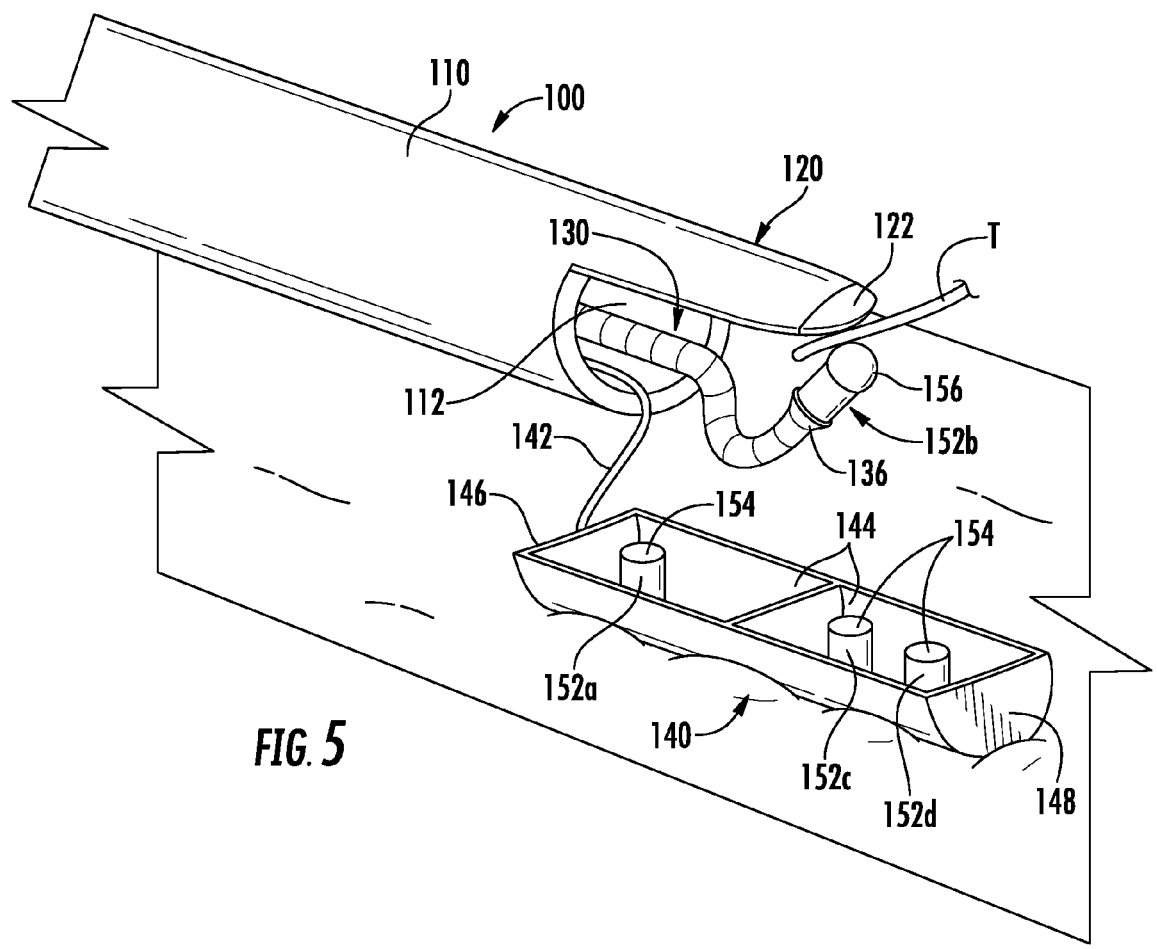
FIG. 5 is a perspective view of the end effector of the electrosurgical instrument of FIG. 4 with the connection arm positioned with a conductive surface of the micro-tip positioned adjacent an energy tip of the end effector.

With reference to FIGS. 3-5, when the toolbox 140 is in the deployed configuration, the connection arm 130 is manipulated to secure the connection end 154 of a respective micro-tip 152a-d to the connection tip 136 of the connection arm 130. The connection end 154 of each micro-tip 152a-d is magnetic such that when the connection tip 136 of the connection arm 130 is activated adjacent one of the connection ends 154, the connection tip 136 magnetically engages the connection end 154 to secure the connection arm 130 to the respective micro-tip 152a-d. When the connection arm 130 is coupled to a respective micro-tip 152a-d, the connection arm 130 is manipulated to remove the respective micro-tip 152a-d from the toolbox 140 such that a treatment portion 156 of the respective micro-tip 152a-d may be used to treat tissue. In embodiments where the connection arm 130 includes the vacuum passage 138, the micro-tips 152a-d may be coupled to the connection tip 136 by the activation of a vacuum source in communication with the vacuum passage 138.

As shown in FIG. 5, the micro-tip 152b, a spherical probe, is secured to the connection arm 130 to treat targeted tissue in accordance with the present disclosure. The connection arm 130 is manipulated to position the micro-tip 152b adjacent the energy tip 122 of the finger 120 with targeted tissue T between the micro-tip 152b and the energy tip 122 of the finger 120. The micro-tip 152b may be used to draw the targeted tissue T towards the energy tip 122. With the targeted tissue T positioned between the energy tip 122 and the micro-tip 152, the electrosurgical energy source 90 is activated to supply electrosurgical energy to the energy tip 122 of the finger 120. The energy tip 122 then delivers the supplied electrosurgical energy to the targeted tissue T. The connection arm 130 is in electrical communication with the electrosurgical energy source 90 (FIG. 1) such that the electrosurgical energy delivered to targeted tissue T with the energy tip 122 is returned to the electrosurgical energy source 90 through the micro-tip 152b and the connection arm 130. In such an embodiment, the end effector assembly 100 delivers electrosurgical energy to targeted tissue T in a bipolar manner.

Alternatively, the electrosurgical energy source 90 may be in electrical communication with a return pad (not shown) that is in contact with the patient such that the end effector 100 delivers electrosurgical energy in a monopolar manner. In such embodiments, the electrosurgical energy delivered to targeted tissue T by the energy tip 122 of the finger 120 is returned to the electrosurgical energy source 90 through the return pad. In such embodiments, the micro-energy tip 122 and/or the connection arm 130 may be electrically isolated from the electrosurgical energy source 90.

After electrosurgical energy is delivered to targeted tissue T, the connection arm 130 may be manipulated to draw additional targeted tissue towards the energy tip 122. After the all the targeted tissue is treated, the connection arm 130 is manipulated to return the micro-tip 152b to the toolbox 140. With the micro-tip 152b returned to the toolbox 140, another micro-tip 152 may be selected and secured to the connection tip 136 of the connection arm 130 to treat targeted tissue.

Figure 6:
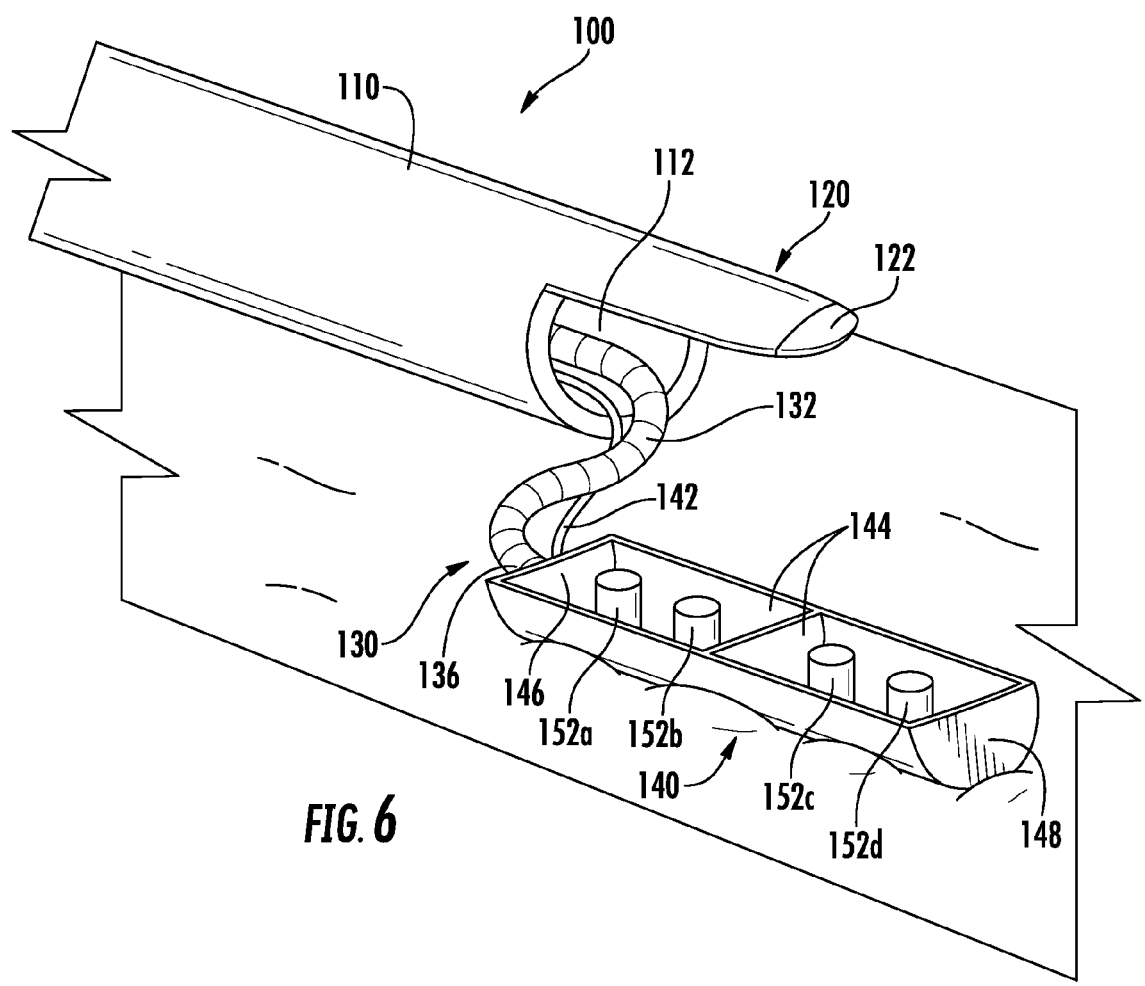
FIG. 6 is a perspective view of the connection arm secured to the toolbox.
Figure 7:
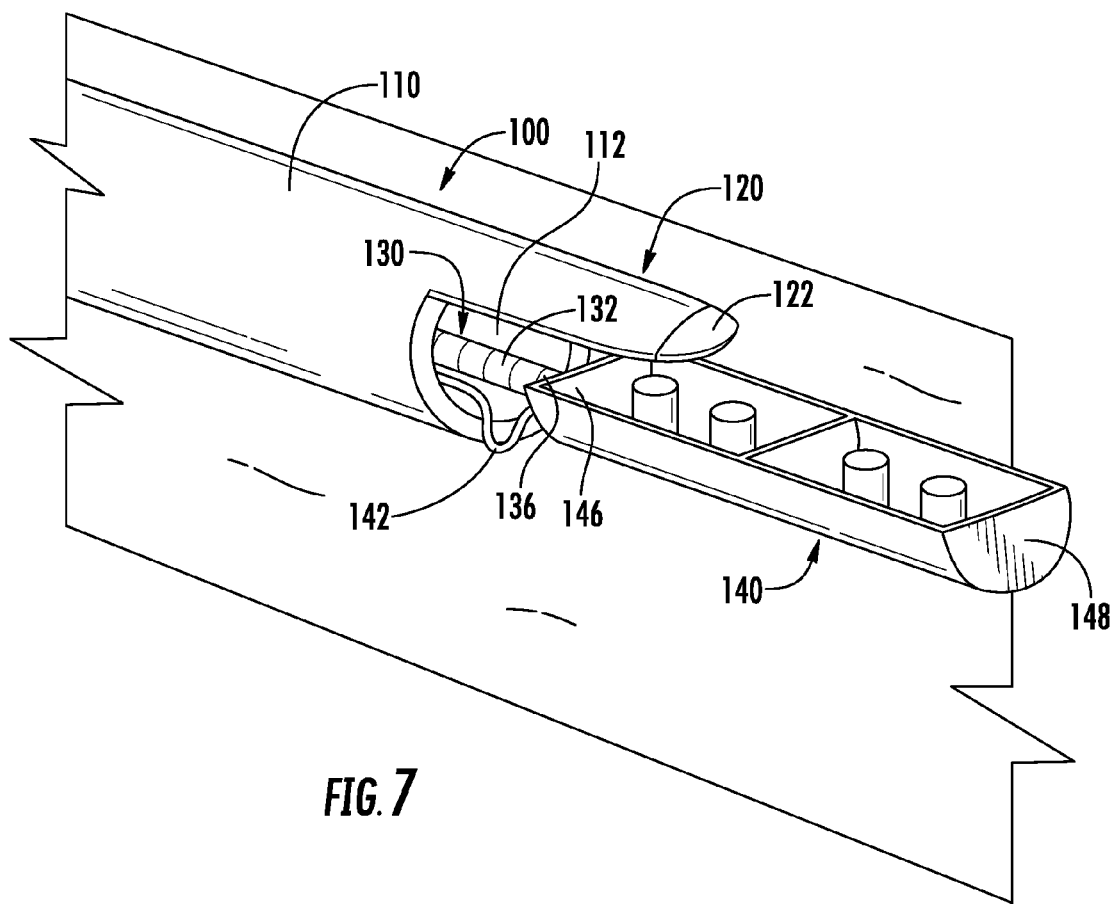
FIG. 7 is a perspective view of the connection arm secured to the toolbox with the toolbox positioned to be retracted from the deployed configuration.
Figure 8A:
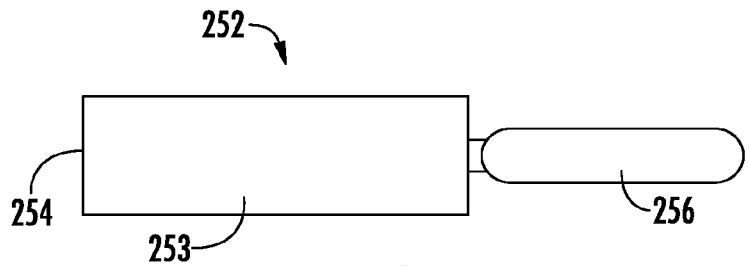
FIGS. 8A-8D are side views of other exemplary micro-tips which may be disposed within the toolbox and securable to the connection arm.
Figure 8B:
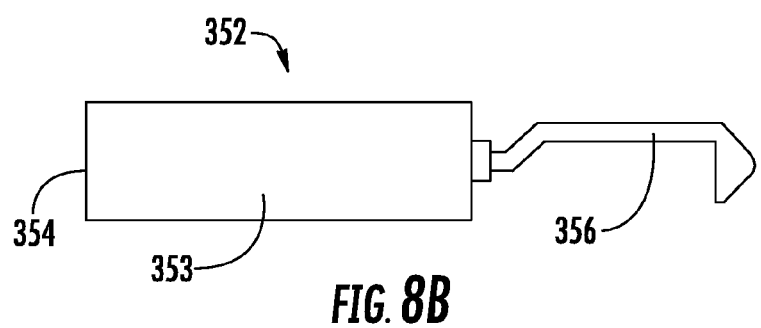
Figure 8C:
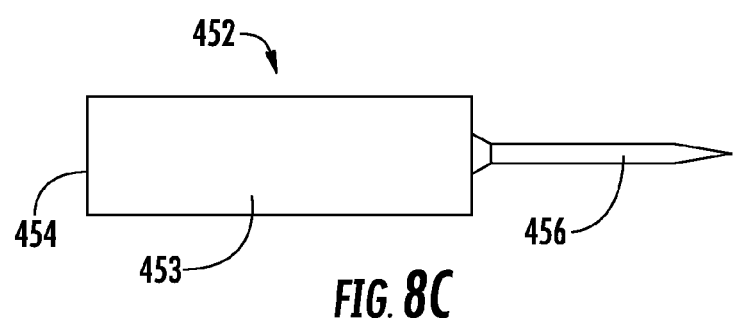
Figure 8D:
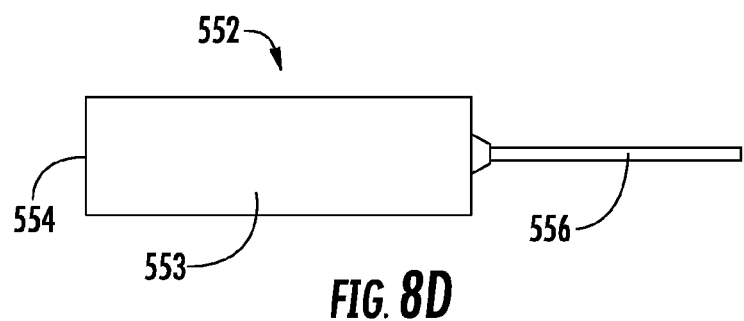

With reference to FIGS. 6 and 7, after all targeted tissue is treated and the micro-tips 152a-d returned to the storage wells 144 of the toolbox 140, the connection arm 130 is used to return the toolbox 140 to the transport configuration. The connection arm 130 is manipulated such that the connection tip 136 is adjacent the proximal wall 146 of the toolbox 140. Then, the connection tip 136 is activated to magnetically engage to the proximal wall 146. With the connection tip 136 of the connection arm 130 secured to the proximal wall 146 of the toolbox 140, the connection arm 130 is manipulated to align the toolbox 140 with the lumen 112 of the tubular portion 110 of the end effector 100 as shown in FIG. 7. With the toolbox 140 aligned with the lumen 112, the connection arm 130 is retracted into the lumen 112 to draw the toolbox 140 into the lumen 112 until the toolbox 140 is in the transport configuration. In the transport configuration, the micro-tips 152-d are retained in the storage wells 144 of the toolbox 140 by a distal wall 148 of the toolbox 140 and the tubular portion 110 even if the micro-tips 152a-d are loose within the storage wells 144.

With reference to FIGS. 8A-D, other micro-tips 252, 352, 452, and 552 are provided in accordance with the present disclosure. Each of the micro-tips 252, 352, 452, 552 is substantially similar to micro-tip 152b and are disposable in the wells 144 (FIG. 3) of the toolbox 140 as detailed above, as such only the differences will be detailed herein. Specifically, micro-tip 252 includes a flat blade 256 that extends from a connection portion 253 which includes a connection end 254 for coupling the micro-tip 252 to the connection arm 130. Micro-tip 352 includes a hook 356 that extends from a connection portion 353 which includes a connection end 354 for coupling the micro-tip 352 to the connection arm 130. Micro-tip 452 includes a pointed shaft 456 that extends from a connection portion 453 which includes a connection end 454 for coupling the micro-tip 452 to the connection arm 130. Micro-tip 552 includes a blunt shaft 556 that extends from a connection portion 553 which includes a connection end 554 for coupling the micro-tip 552 to the connection arm 130.

Before a surgical procedure, the toolbox 140 may be loaded with one or more of each of the micro-tips 152a-d, 252, 352, 452, 552. As shown in FIG. 3, the toolbox 140 is loaded with four micro-tips; however, the toolbox 140 may be loaded with more or less than four micro-tips. During a surgical procedure, a clinician selects a micro-tip 152b, 252, 352, 452, 552 from the toolbox 140 based on the needs of the surgical procedure. By allowing a clinician to change micro-tips during a surgical procedure, the number of instrument changes may be reduced during a surgical procedure with may reduce the time and thus, the cost of a surgical procedure.

Figure 9:
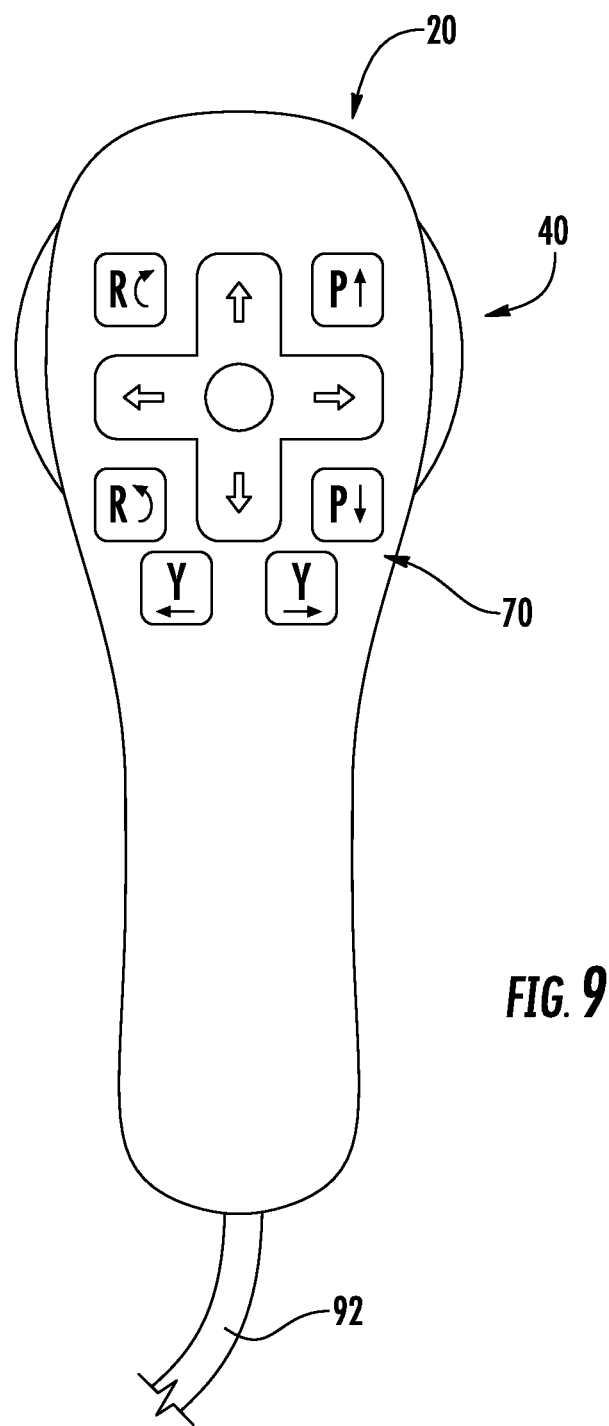
FIG. 9 is a rear view of the housing of the surgical instrument illustrating a control interface for manipulating the connection arm.

Referring to FIGS. 1 and 9, the housing 20 may include a control interface 70 for manipulating the connection arm 130. The control interface 70 manipulates the connection arm 130 through six degrees of freedom ("6 DOF") and may selectively activate the connection tip 136. Additionally or alternatively, the electrosurgical system 1 may include a remote interface (not shown) to manipulate the connection arm 130 through 6 DOF and to selectively activate the connection tip 136.

Figure 10:
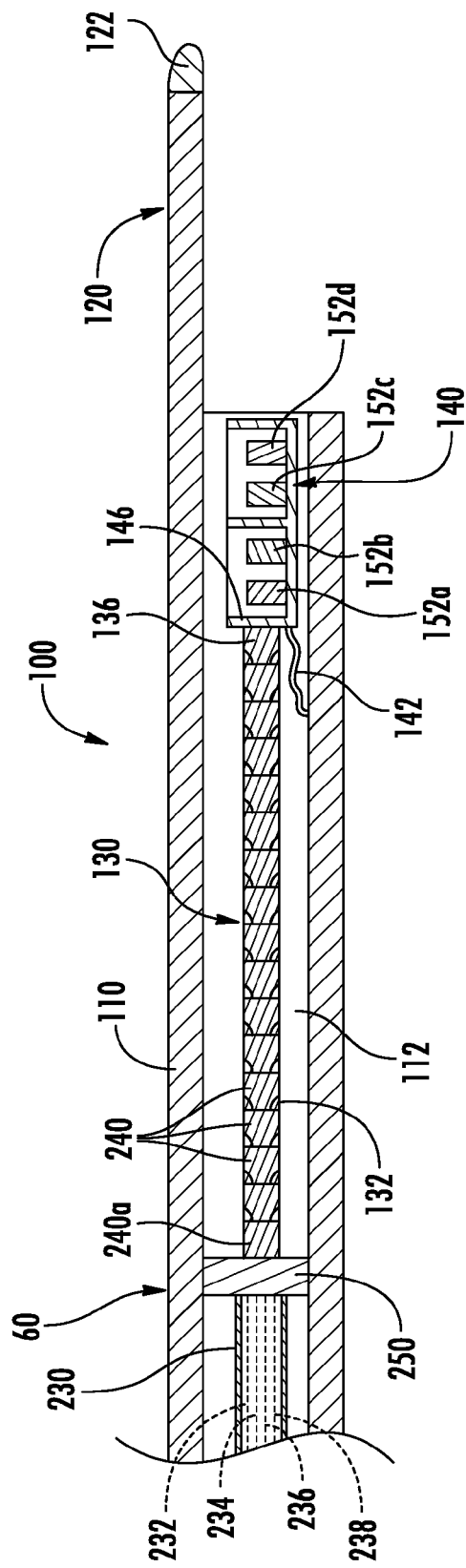
FIG. 10 is a cross-sectional view taken along the section line 10-10 of FIG. 2.

With additional reference to FIG. 10, the connection arm 130 can be manipulated by drive cables 232, 234, 236, 238 which extend through a hollow tube 230, which is disposed within the shaft 60, and segments 240 of the connection arm 130. The drive cables 232, 234, 236, 238 may be associated with drive motors 98 positioned within the housing 20 and controlled by the control interface 70 or may be associated with manual drive assemblies disposed on the housing (not shown). Examples of such drive cables, segments, and manual drive assemblies are disclosed in U.S. Patent Publication No. 2012/0022325 and U.S. Pat. Nos. 8,475,453 and 8,721,640. Examples of such drive motors are disclosed in International Patent Application No. PCT/US15/14542. The entire contents of each of these disclosures are incorporated herein by reference.

A proximal segment 240a of the connection arm 130 can be mounted to a flange 250 that is translatable within the shaft 60 to extend and retract the connection arm 130. The flange 250 can be manipulated to rotate the connection arm 130 and can also be manipulated to move the connection arm 130 about a pitch and yaw axis. Specifically, the hollow tube 230 can be extended, retracted, and rotated relative to the shaft 60 to translate and rotate the flange 250. Examples of such a mounting flange are disclosed in U.S. Pat. No. 6,231,565, the entire contents of this disclosure are incorporated herein by reference.

It is contemplated that all or portions of the toolbox 140 and the micro-tips micro-tips 152a-d, 252, 352, 452, 552 may be constructed of bioabsorbable materials.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope of the claims appended hereto.

What is claimed:

1. A surgical instrument comprising:
    a housing;
    a shaft extending from the housing; and
    an end effector assembly disposed at a distal end of the shaft, the end effector assembly including:
        a tubular portion defining a lumen;
        a connection arm extendable from the lumen of the tubular portion and having a connection tip; and
        a toolbox having a micro-tip that is configured to be selectively secured to the connection tip of the connection arm, the toolbox having a transport configuration where the toolbox is disposed within the lumen of the tubular portion and a deployed configuration where the toolbox is disposed entirely outside of the lumen, the connection tip configured to releasably couple to the toolbox such that the connection arm is configured to retract the toolbox into the lumen to transition the toolbox from the deployed configuration to the transport configuration when the connection tip is coupled to the toolbox.

2. The surgical instrument according to claim 1, wherein in the deployed configuration of the toolbox, a connection end of the micro-tip is engagable by the connection tip of the connection arm.

3. The surgical instrument according to claim 2, wherein the connection tip of the connection arm is securable to the connection end of the micro-tips.

4. The surgical instrument according to claim 3, wherein the connection tip includes an electromagnet.

5. The surgical instrument according to claim 1, wherein the micro-tip is removable from the toolbox.

6. The surgical instrument according to claim 1, wherein the toolbox includes a plurality of micro-tips, each micro-tip of the plurality of micro-tips is selectively securable to the connection arm.

7. The surgical instrument according to claim 1, wherein the connection arm is moveable in six degrees of freedom.

8. The surgical instrument according to claim 7, wherein the housing includes a control interface for manipulating the connection arm.

9. The surgical instrument according to claim 1, wherein the connection arm secures the toolbox in the transport configuration.

10. The surgical instrument according to claim 1, wherein the connection arm is extendable to transition the toolbox from the transport configuration to the deployed configuration.

11. The surgical instrument according to claim 1, wherein the end effector includes a finger distally extending from the tubular portion to an energy tip, the energy tip configured to deliver electrosurgical energy to tissue.

12. The surgical instrument according to claim 11, wherein the connection arm is configured to return electrosurgical energy from the energy tip when the micro-tip is coupled to the connection tip.

13. The surgical instrument according to claim 4, wherein the electromagnet is selectively energizable to couple the connection tip to the toolbox or the micro-tip.

14. The surgical instrument according to claim 1, wherein the connection tip defines a vacuum passage therethrough, the connection tip configured to releasably couple to the toolbox or the micro-tip by a vacuum provided through the vacuum passage.

15. A surgical system comprising:
    an electrosurgical energy source;
    a surgical instrument including a housing and a shaft extending from the housing; and
    an end effector assembly disposed at a distal end of the shaft, the end effector assembly including:
        a tubular portion defining a lumen;
        a finger extending distally from the tubular portion and including an energy tip in electrical communication with the electrosurgical energy source and configured to deliver electrosurgical energy to tissue;
        a connection arm extendable from the lumen of the tubular portion and having a connection tip; and
        a toolbox having a micro-tip configured to be selectively secured to the connection tip of the connection arm, the toolbox having a transport configuration where the toolbox is disposed within the lumen of the tubular portion and a deployed configuration where the toolbox is disposed entirely outside of the lumen, the connection tip of the connection arm configured to releasably couple to the toolbox such that retraction of the connection arm into the lumen transitions the toolbox from the deployed configuration to the transport configuration when the connection tip is coupled to the tool box.

16. The surgical system according to claim 15, wherein the end effector assembly is configured to deliver electrosurgical energy in a bipolar manner.

17. The surgical system according to claim 16, wherein the connection arm is configured to return electrosurgical energy from the energy tip to the electrosurgical energy source when the micro-tip is secured to the connection tip.

18. A method for treating tissue, the method comprising:
extending a connection arm from a lumen defined by a tubular portion of an end effector assembly to deploy a toolbox from a transport configuration, wherein the toolbox is disposed within the lumen, to a deployed configuration, wherein the toolbox is disposed outside of the lumen;
removing a micro-tip from the toolbox with the connection arm;
manipulating the connection arm to position targeted tissue adjacent an energy tip disposed at a distal end of a finger distally extending from the tubular portion of the end effector;
delivering electrosurgical energy to the targeted tissue with the energy tip;
coupling the connection arm to the toolbox; and
retracting the connection arm with the toolbox coupled thereto into the lumen to return the toolbox to the transport configuration.

19. The method according to claim 18, further comprising activating a connection tip of the connection arm to secure the toolbox to the connection tip before retracting the connection arm into the lumen.

20. The method according to claim 18, wherein removing the micro-tip from the toolbox includes engaging a connection end of the micro-tip with a connection tip of the connection arm and activating the connection end to secure the micro-tip to the connection tip.

* * * * *